United States Patent [19]

Hamill

[11] Patent Number: 4,728,502

[45] Date of Patent: Mar. 1, 1988

[54] APPARATUS FOR THE CHEMICAL SYNTHESIS OF OLIGONUCLEOTIDES

[76] Inventor: Brendan J. Hamill, 11, Napier Square, Livingston EH54 5DG, Scotland

[21] Appl. No.: 727,446

[22] Filed: Apr. 26, 1985

[30] Foreign Application Priority Data

May 2, 1984 [GB] United Kingdom ............... 8411301
Mar. 4, 1985 [GB] United Kingdom ............... 8505448

[51] Int. Cl.$^4$ .............................................. C07K 1/04
[52] U.S. Cl. .................................... 422/116; 422/62; 422/134; 422/191; 422/209; 435/287; 435/289; 436/89; 935/88
[58] Field of Search ....................... 422/62, 68, 70, 71, 422/131, 134, 116, 171, 177, 180, 191, 129, 209; 436/55, 89, 90, 94; 435/287, 288, 289; 935/88; 210/489, 498

[56] References Cited

U.S. PATENT DOCUMENTS

| | | | |
|---|---|---|---|
| 2,792,122 | 5/1957 | Munch et al. | 210/489 |
| 3,490,879 | 1/1970 | Urban | 422/209 |
| 4,152,391 | 5/1979 | Cabrera | 422/103 |
| 4,159,950 | 7/1979 | Hayashida et al. | 210/498 |
| 4,267,045 | 5/1981 | Hoof | 210/498 |
| 4,507,977 | 4/1985 | Cabrera | 422/103 |
| 4,517,338 | 5/1985 | Urdea | 422/131 |

FOREIGN PATENT DOCUMENTS

05672 1/1982 European Pat. Off. .

OTHER PUBLICATIONS

"Rapid Synthesis of Oligodeoxyribonucleotides VII. Solid Phase Synthesis . . . Kieselguhr–Polyamide Support", by M. J. Gait et al., Nucleic Acids Research, vol. 10, No. 20, Oct. 25, 1982.

Primary Examiner—Michael S. Marcus
Attorney, Agent, or Firm—Shoemaker and Mattare, Ltd.

[57] ABSTRACT

Apparatus for carrying out a multiplicity of different sequential chemical syntheses on solid-supports simultaneously comprises a multiplicity of complementary support plates each formed with a reaction chamber opening through the plate and containing the solid-support together with at least one by-pass channel through the plate. The by-pass channel or channels and reaction chamber are disposed equi-angularly and at the same radial distance about an axis of the plate. The plates are rotatably supported in compression in face to face contact between end plates complementary to the plates and each formed with a blank position and passages for at least one reactant stream. Means is provided for independently rotating each plate whereby each reaction chamber of each plate may independently be isolated or positioned in the or a selected reactant stream.

5 Claims, 6 Drawing Figures

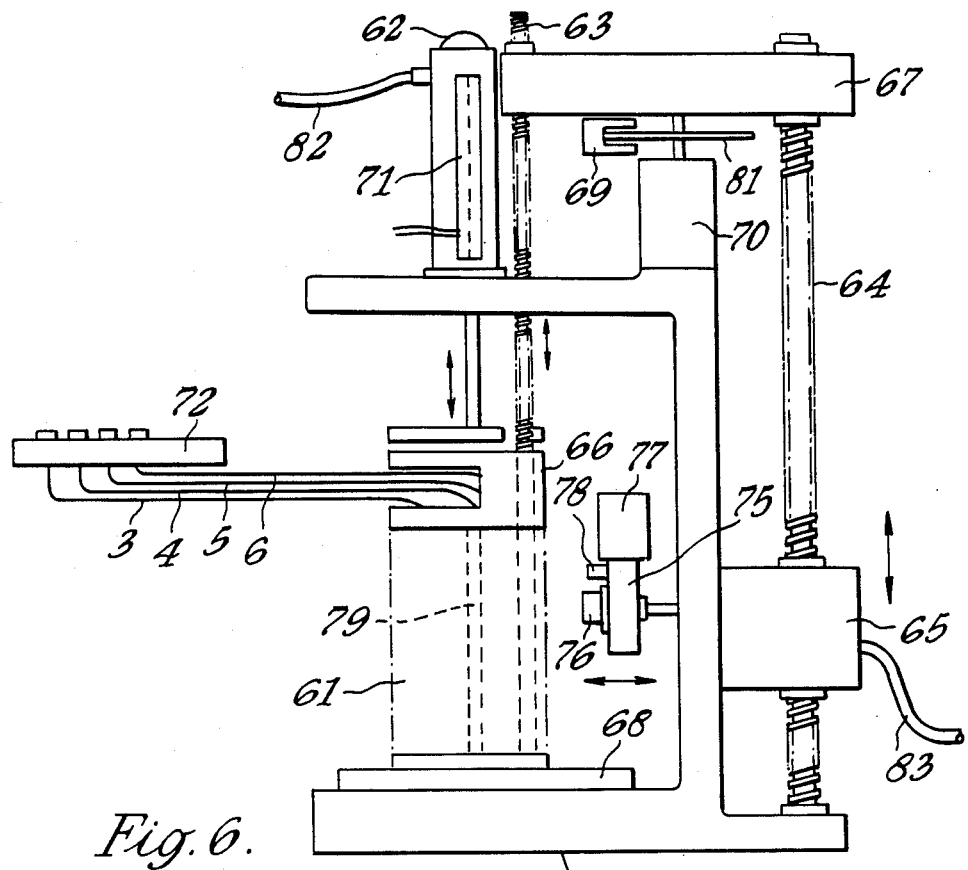
Fig. 6.
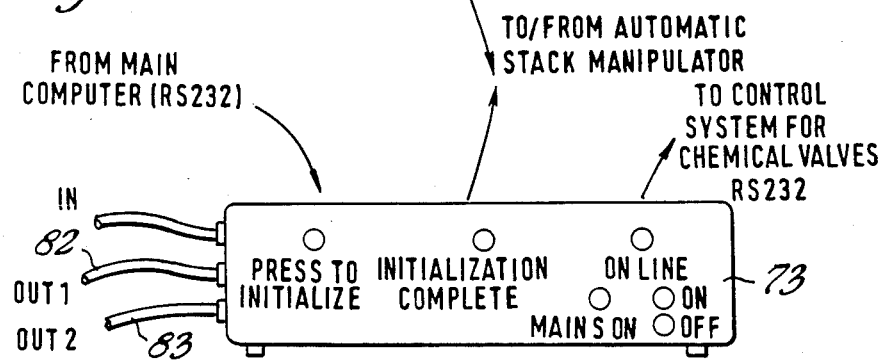

_4,728,502_

APPARATUS FOR THE CHEMICAL SYNTHESIS OF OLIGONUCLEOTIDES

FIELD OF THE INVENTION

This invention relates to an apparatus for the chemical synthesis of oligonucleotides.

BACKGROUND OF THE INVENTION

It is known from Letsinger et al, Nucleic Acids Research 1975, vol. 2, pages 773–786, that oligonucleotides may be chemically synthesised by the sequential addition of suitably elaborated nucleoside derivatives to a shorter oligonucleotide which is covalently linked to a solid polystyrene support. Other types of solid support have also been used for this purpose, for example, cellulose, as described by Crea and Horn, Nucleic Acids Research 1980, vol. 8, pages 2331–2348, polyacrylamide, as described by Gait et al, Nucleic Acids Research, 1982, vol. 10, pages 6243–6254, silica, as described by Caruthers et al, Tetrahedron Letters, 1980, vol. 21, pages 719–722, and controlled-pore glass, as described by Sproat et al, Tetrahedron Letters, 1983, vol. 24, pages 5771–5774. In these known methods, the simultaneous synthesis of several different oligonucleotides can be accomplished only by performing each synthesis independently, thus demanding considerable investment in equipment and operator time.

Simultaneous synthesis of several different oligonucleotides has been described by Frank et al, Nucleic Acids Research, 1983, vol. 11, pages 4365–4377, using cellulose discs as the solid support. However, this method is very laborious in that each individual disc must be dried and sorted at the conclusion of each stage of the synthesis, and thereafter transferred to the appropriate reaction vessel prior to the next stage. This complex procedure enhances the probability of failure of a synthesis caused by moisture absorption during handling, or by operator error during the sorting process. In addition, the quantity of each oligonucleotide that may be prepared in any single synthesis is limited by the capacity of the cellulose disc used. Furthermore, the method is only capable of applicatin to synthetic methods employing solid support materials which can readily be formed into coherent, mechanically stable discs.

SUMMARY OF THE INVENTION

I have now found that the simultaneous synthesis of several different oligonucleotides may be accomplished, advantageously in a convenient and rapid manner amenable to automation, by use of a suitable apparatus.

According to the present invention, there is provided an apparatus which comprises a series of plates clamped together, each of which plates may be moved independently of the others, and each of which plates contains a reaction chamber equipped with an inlet and outlet for the passage of fluids, and each of which plates also contains a number of fluid passages, the fluid passages and reaction chamber in each plate being constructed in such a way as to allow, when all the plates are suitably aligned, passage of at least four different fluid streams through all the plates of the apparatus, irrespective of the orientation of the reaction chamber in any individual plate relative to the orientation of the reaction chamber in any other plate in the apparatus.

The invention further provides apparatus for carrying out a multiplicity of different sequential chemical syntheses on solid-supports simultaneously comprising a multiplicity of complementary support plates each formed with a reaction chamber opening through the plate and containing the solid-support together with at least one by-pass channel through the plate, said by-pass channel or channels and reaction chamber being disposed equi-angularly and at the same radial distance about an axis of the plate, said plates being rotatably supported in compression in face to face contact between end plates complementary to the plates and each formed with a blank position and passages for at least one reactant stream, and means for independently rotating each plate whereby each reaction chamber of each plate may independently by isolated or positioned in the or a selected reactant stream.

The invention yet further provides a method for carrying out a multiplicity of different chemical syntheses simultaneously which comprises providing apparatus as aforesaid and for each step adjusting the positions of the plates according to the compounds to be synthesised, applying pressure to the plates, passing reactant streams through the plates and releasing said pressure to permit the plate positions to be adjusted in the next following step.

BRIEF DESCRIPTION OF DRAWINGS

Specific embodiments of the invention will now be described, by way of example, with reference to the accompanying drawings, in which:

FIG. 6 shows diagrammatically an apparatus with automatically rotated plates.

DETAILED DESCRIPTION OF PREFERRED EMBODIMENTS

Figure 1:
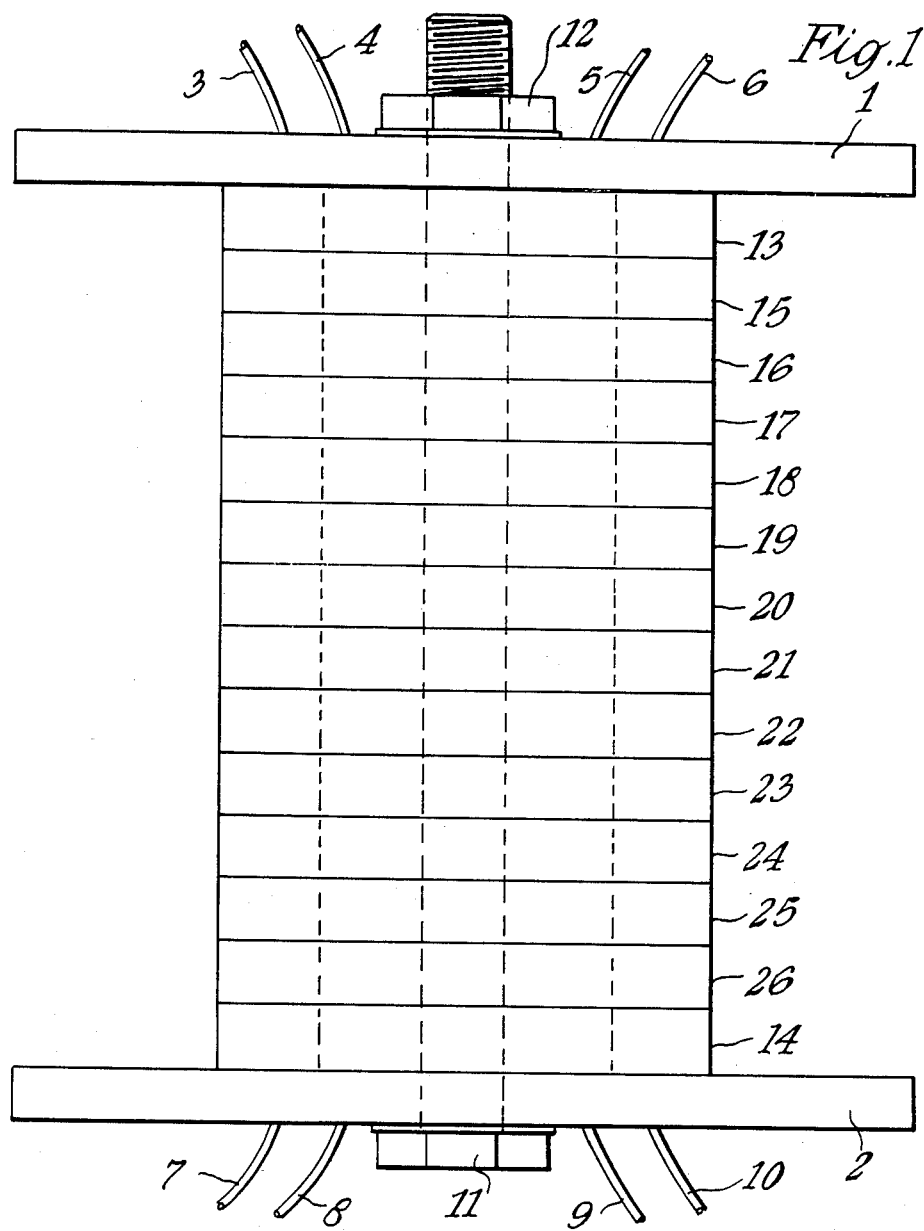
FIG. 1 shows in side view the assembled apparatus.
Figure 2:
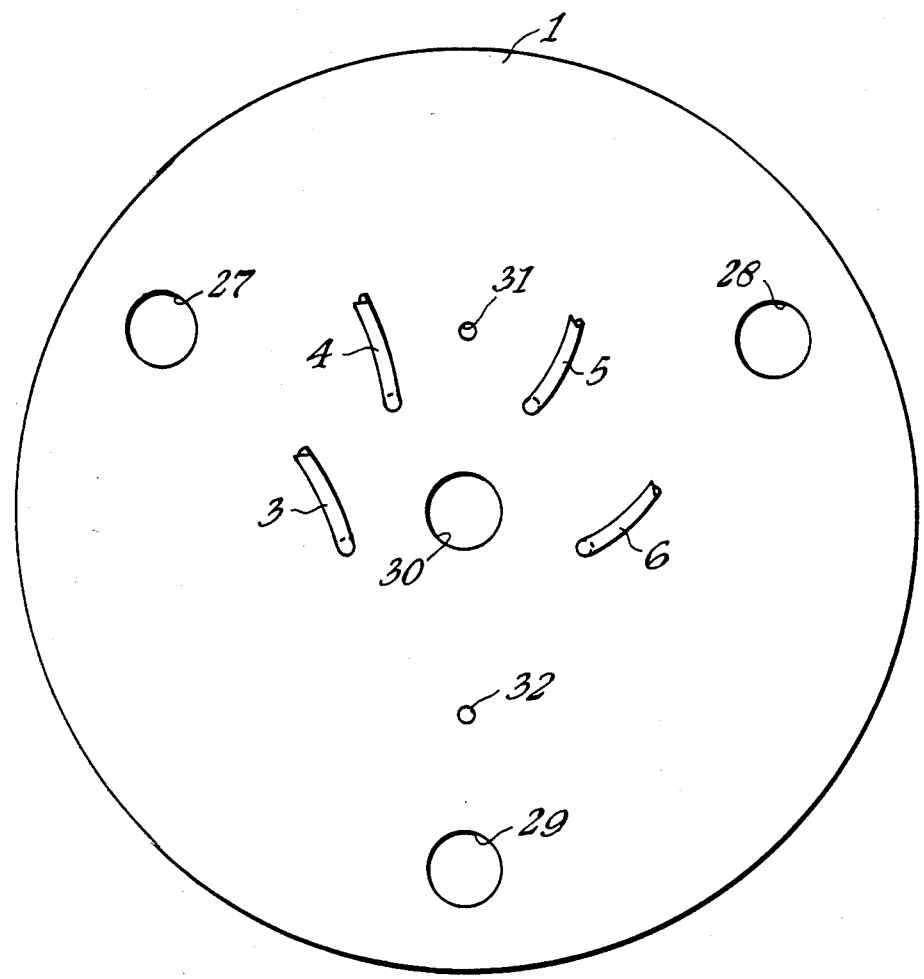
FIG. 2 shows in plan view one of the end-plates of the apparatus.
Figure 3:
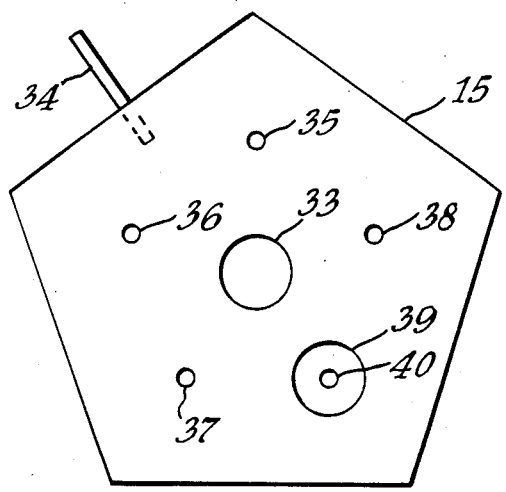
FIG. 3 shows in plan view one of the movable plates of the apparatus.
Figure 4:
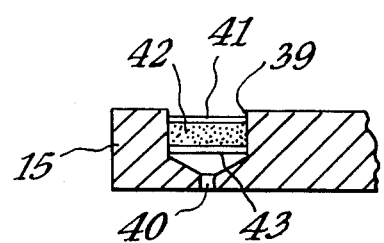
FIG. 4 shows in cross-section the construction of the reaction chamber in the movable plates.
Figure 5:
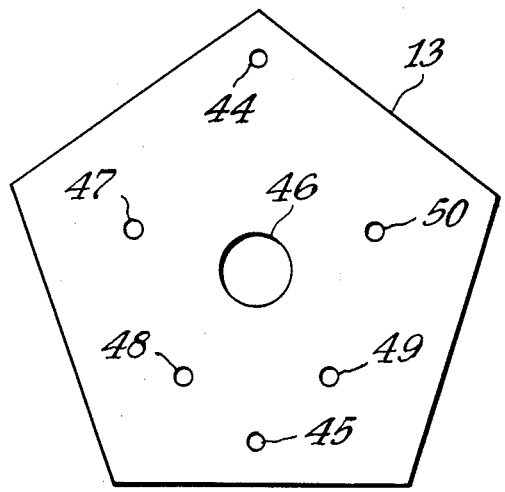
FIG. 5 shows in plan view one of the fixed plates of the apparatus.

Referring to the drawings, the apparatus comprises two end-plates 1, 2 to each of which are attached tubes 3, 4, 5, 6 and 7, 8, 9, 10 for the passage of fluids through the apparatus, two fixed plates 13, 14 which engage in locating pins 31, 32 on the end-plates 1, 2 by means of drilled holes 44, 45 so that the fluid passages 47, 48, 49, 50 align with the tubes 3, 4, 5, 6 of the end-plate 1, and twelve rotating plates 15–26 inclusive fitted between the two fixed plates, the whole assembly being held together by a clamp bolt 11 and nut 12 passing through the central holes 30, 33 and 46 of the individual components.

Each rotating plate 15–26 contains four fluid passages 35, 36, 37, 38 and a reaction chamber 39 equipped with a fluid outlet 40, all arranged symmetrically about the central hole 33, and is equipped with a pin 34 by means of which the plate may be rotated about the central bolt 11.

When the apparatus is in use, the reaction chamber 39 contains a solid-support material 42 held in place by porous discs 41, 43.

Preferred materials for the construction of the components of the apparatus are stainless steel for the end-plates 1, 2 and the pin 34, polytetrafluoroethylene for the plates 13, 14, 15-26 and porous discs 41, 43 and either of these materials for the tubes 3-10 inclusive.

Additional clamp bolts may be fitted between the holes 27, 28, 29 of the end plates to facilitate operation at high fluid pressures.

The number of rotating plates in the apparatus may be increased or reduced according to requirements.

In use, the apparatus is connected by means of the tubes 3, 4, 5, 6 to four fluid streams containing, in solution, suitably elaborated derivatives of the four common nucleosides, together with any necessary catalyst or activating agent.

At each stage of the synthesis, each rotating plate 15-26 of the apparatus is aligned so that the solid-support material 42 contained in the reaction chamber 39 contacts whichever of the four fluid streams is appropriate to the synthesis of the particular oligonucleotide being prepared on the solid-support material 42 contained in that plate. Alternatively, any of the rotating plates 15-26 may be aligned in a fifth position in which the solid-support material 42 in that plate is isolated from all four fluid streams. This feature provides for the simultaneous synthesis of oligonucleotides containing different numbers of nucleoside units, by allowing further elongation of some oligonucleotide chains without affecting thos which have already been completed. Alignment of each rotating plate 15-26 of the apparatus may be performed manually or by use of a mechanical positioning device. In the latter case, the apparatus may form part of a device which performs all synthetic operatins automatically.

The apparatus may be applied to the synthesis of both Ribonucleic acid and Deoxyribonucleic acid molecules by use of appropriate nucleoside derivatives during the synthesis. It may be adapted to the synthesis of other types of biological molecules which can be synthesised by stepwise addition of units to a solid-support, for example oligopeptides and oligosaccharides.

A version of the apparatus with automatic angular adjustment of the individual discs is shown in FIG. 6. The stack of discs 61 rotatably supported on a central stainless steel Teflon coated spindle 79 stands on a Teflon base 68 that located the discs and is provided with a fluid outlet. A protective stack header 66 allows feed tubes 3-6 from an injectin port 72 to deliver reactant to the four flow channels through the stack. Each disc in the stack is about 40 mm in diameter and about 6 mm thick and when under no pressure they are freely rotatable on the spindle 79. The approximate angular position of each disc is indicated by a dot code formed by coloured Teflon inserts on the disc edge. All the discs may be working discs formed with four holes 35-38 and a reaction chamber 39 but if desired the height may be made up by dummy discs having five through holes and free from coloured coding inserts. Each disc has its edge surface slightly knurled for good grip with a friction drive wheel (described below).

A pneumatic pressure cylinder 62 presses downwardly onto the header 66 to provide the compressive force needed to seal the disc to disc interfaces once the positions of the individual discs have been properly arranged. The actual force is controlled by an air pressure regulator and the travel of the piston is determined by a magnetically operated piston position sensor array 71 or a linear port to give an accuracy ±0.1 inches (0.25 cms) which is sufficient to confirm the number of discs in the stack 61 and thereby to define the number of vertical positions through which a disc rotation mechanism has to pass to position each disc in the stack 61. The cylinder 62 is preferably of the spring return type and the miniature valves for controlling the compressed air are suitably incorporated into an interface box 73. It is understood that the cylinder 62 is operated to maintain pressure on the disc stack 61 while reactants are being passed, but that it is retracted to relieve the pressure while the position of the discs in the discs in the stack is being changed for the next following synthesis step.

A body 65 of a disc rotation mechanism is supported for vertical movement on a worm drive rod 64 which is rotated by motor 70 and gearbox 67 which includes a cogged belt driving a wheel (not shown) engaged with the rod 64. The shaft of the motor 70 carries an encoder disc 81 movement of which is monitored by sensor 69 to enable the distance through which the body 65 has moved to be ascertained. The motor 70 may be a stepping motor or a geared DC motor. The discs in the stack 61 are each formed with an extra 5 quarter inch (0.6 cm) holes in their periphery to permit a location pin 63 to pass through. The pin 63 is also worm driven from the motor 70 via the gearbox 67 and cogged belt, and the gearbox 67 ensures a direct 1:1 relationship between the vertical travel of the pin 63 and the body 65. The cogged rubber belt transmission requires no lubrication and is self-adjusting by means of a spring loaded jockey wheel. The rod 63 is at its lower end in the form of a quarter inch (0.6 cm) Teflon coated tapered rod that is moved stepwise downwardly one disc thickness behind the body 65 so that the disc whose position has just been adjusted together with any overlying discs is immobilised during adjustment of the angular position of the next following disc. Locking is by passage of the rod 63 through the quarter inch (0.6 cm) diameter peripheral holes in the disc stack 61.

The body 65 on the rod 64 includes an air operated ram that moves a drive assembly 75 to and from engagement with a selected disc in the stack 61. An electric motor 77 and gearbox drive a drive wheel 76 that engages the edge of the selected disc to effect rotation thereof, a disc position photocell 78 counting the disc edge dot code to monitor disc position. When the correct disc position has been detected, the assembly 75 is retracted after which the motor 70 is energised to engage the pin 63 with the newly positioned disc and to index the assembly 75 into engagement with the next disc to be positioned.

The interface unit 73 provides pneumatic lines 82, 83 to the cylinder 62 and to the cylinder in body 65 and contains logic units to enable the apparatus to be initialised. Thus the cylinder 62 will be operated once to allow the number of discs in the stack 61 to be sensed. A control channel such as an RS 232 port is provided for interface with a host computer to provide for positioning instructions for the several discs. The host computer will also control the chemical supply via injection ports 72. Internal DIP switches may be provided to adjust the baud rate parity and other parameters of the RS 232 port.

I claim:

1. Apparatus for simultaneously carrying ot a multiplicity of different chemical and biochemical syntheses on solid supports comprising a multiplicity of support plates each formed with passageways therethrough, one of said passageways through each plate containing a reaction chamber having a solid support; said other passageways each providing a by-pass channel without a solid support, said by-pass channels and reaction chamber being disposed equi-angularly and at the same radial distance about an axis of each plate, means for holding said plates in rotatable alignment about said axis in compression and in face-to-face fluid tight relationship, holding means including end plates complementary to the plates and each formed with a blank position and passages for at least one reactant stream, and means for independently rotating each plate whereby each rotation chamber of each plate may be isolated from or positioned in a selected reactant stream.

2. Apparatus which comprises a series of plates clamped together, means for moving each plate relative to the others, one reaction chamber in each plate which chamber is equipped with an inlet and outlet for the passage of fluids and including a solid support material between said inlet and outlet; each plate also containing a plurality of other fluid passageways without solid support; and means for aligning each plate so as to allow passage of different fluid streams through the passageways in the series of plates, irrespective of the orientation of the reaction chamber in any individual plate relative to the orientation of the reaction chamber in any other plate in the apparatus.

3. Apparatus according to claim 2 provided with means for interfacing with a computer.

4. Apparatus according to claim 3 wherein the computer controls supply of fluids to the fluid passages.

5. Apparatus according to claim 4 wherein the computer further controls the alignment of the plates.

* * * * *